(12) United States Patent
Sidebotham et al.

(10) Patent No.: US 8,518,044 B2
(45) Date of Patent: Aug. 27, 2013

(54) DISPOSABLE FLEXIBLE REAMER SHAFT FOR MEDICAL APPLICATIONS

(76) Inventors: Christopher G. Sidebotham, Mendham, NJ (US); Randall J. Lewis, Bethesda, MD (US); Leon Roitburg, East Hanover, NJ (US)

( * ) Notice: Subject to any disclaimer, the term of this patent is extended or adjusted under 35 U.S.C. 154(b) by 482 days.

(21) Appl. No.: 12/586,876

(22) Filed: Sep. 29, 2009

(65) Prior Publication Data
US 2010/0152739 A1    Jun. 17, 2010

Related U.S. Application Data

(63) Continuation-in-part of application No. 12/583,873, filed on Aug. 27, 2009, which is a continuation-in-part of application No. 12/072,671, filed on Feb. 27, 2008, which is a continuation-in-part of application No. 11/973,260, filed on Oct. 5, 2007, which is a continuation-in-part of application No. 11/704,754, filed on Feb. 9, 2007.

(51) Int. Cl.
*A61B 17/00* (2006.01)

(52) U.S. Cl.
USPC .......................................................... 606/80

(58) Field of Classification Search
USPC ................................. 606/79–81, 84
See application file for complete search history.

(56) References Cited

U.S. PATENT DOCUMENTS

| | | | |
|---|---|---|---|
| 3,554,192 A | 1/1971 | Isberner | 606/80 |
| 4,362,520 A | 12/1982 | Perry | 464/149 |
| 4,541,423 A | 9/1985 | Barber | 606/80 |
| 4,706,659 A | 11/1987 | Matthews et al. | 606/80 |
| 4,751,922 A | 6/1988 | DiPietropolo | 606/80 |
| 4,793,363 A * | 12/1988 | Ausherman et al. | 600/567 |
| 5,122,134 A | 6/1992 | Borzone et al. | 606/80 |
| 5,720,749 A * | 2/1998 | Rupp | 606/79 |
| 5,906,606 A * | 5/1999 | Chee et al. | 604/527 |
| 5,908,423 A | 6/1999 | Kashuba et al. | 606/80 |
| 6,015,411 A * | 1/2000 | Ohkoshi et al. | 606/80 |
| 6,471,709 B1 * | 10/2002 | Fawzi et al. | 606/114 |

FOREIGN PATENT DOCUMENTS

| | | |
|---|---|---|
| EP | 0253526 | 1/1988 |
| WO | WO03/039378 | 5/2003 |

OTHER PUBLICATIONS

NT Flexible Reamer Shaft for Orthopaedic Application at, http://www.fitec.co.jp/ftm/english/nt-e/reamer.htm.

* cited by examiner

*Primary Examiner* — Anu Ramana
(74) *Attorney, Agent, or Firm* — Ernest D. Buff; Ernest D. Buff & Associates LLC; Dave Narasimhan (57) ABSTRACT

A low cost disposable flexible reamer shaft has a flexible cylindrical braided tube shaft with an outer diameter in the range of 4 to 14 millimeters and 250 to 400 mm length, and a central aperture for insertion of a flexible polymeric tube. The braided tube shaft is permanently attached to a first end element and a second end element. The threaded end of the first end element attaches to female threads of modular tapered, cylindrical or spherical, hollow or solid reamer assembly. The second end element fits into a chuck of a drive motor. The threaded attachment of the first end provides local centerline matching. A guide pin is inserted in the bone cavity, which enters the reamer. The central aperture of the flexible polymeric tube provides centerline matched, wobble-free reaming. The reaming end point is precisely the guide pin inserted location while the reaming direction is controlled by the surgeon by flexing the flexible reamer shaft.

12 Claims, 5 Drawing Sheets

DISPOSABLE FLEXIBLE REAMER SHAFT FOR MEDICAL APPLICATIONS

This is a Continuation-In-Part of application Ser. No. 12/583,873, filed on Aug. 27, 2009 for "Disposable Reamer Shaft For Modular, Spherical, or Tapered Hollow Reamer Assembly For Medical Applications" which, in turn, is a Continuation-In-Part of application Ser. No. 12/072,671, filed on Feb. 27, 2008 for "Modular Spherical Hollow Reamer Assembly For Medical Application" which is a Continuation-In-Part of application Ser. No. 11/973,260, filed Oct. 5, 2007 for "Modular Tapered Hollow Reamer For Medical Applications" which, in turn, is a Continuation-In-Part of application Ser. No. 11/704,754, filed Feb. 9, 2007, the disclosures of which are hereby incorporated in their entirety by reference thereto.

BACKGROUND OF THE INVENTION

1. Field of the Invention

The present invention relates to surgical reamers that create bone cavities; and, more particularly, to a flexible disposable reamer shaft that may be attached to a modular disposable spherical or tapered hollow reamer, the disposable reamer shaft being concentrically attached to a modular hollow reamer to provide wobble-free rotation of the reamer tool.

2. Description of the Prior Art

Reaming of the internal canal of bones is required in many surgical procedures of orthopedic surgery. These procedures include hip replacement and shoulder replacement, and the like. Reamers are used in procedures that involve creation of acetabular bone cavities that accept a properly sized acetabular cups. Surgical reamers are used in orthopedic surgery to enlarge medullary canals of long bones such as the femur and humerus in preparation for insertion of fixation devices, performing an intramedullary osteotomy, stimulating bone growth. The medullary canals of bones are seldom straight. More typically, the canal will have some degree of curvature to it. Should a straight and rigid series of reamers be employed to enlarge the canal, there is considerable likelihood that the reamer, if not being capable of following the bone's curvature, will jam or will not remove the desired uniform amount of bone tissue. In such a situation excessive tissue removal occurs in at least one plane as a reamer advances. For this reason, medullary canals are almost always prepared with reamers having a flexible shaft. Generally reamers for use with a flexible shaft utilize a central bore through both the reamer and drive shaft. The central bore is intended to receive a long, small diameter guide pin, which is initially inserted into the medullary canal to act as a track for the advancing reamer. However, the use of a flexible shaft does not always solve the problem of excessive tissue removal and jamming. When this jamming occurs with the prior art cutting head, the long guide pin has to be withdrawn from its position to assist in dislodging the reamer cutting head. This can result in a loss of reduction at the fracture site. Heretofore, the shape of the reamer cutting heads has been basically a cylinder with a short angled area towards the front that would do the cutting and another short angled area at the back of the head that is intended to facilitate the removal of the reamer. Therefore, the flexible reamer shaft has to connect to a tapered hollow reamer or a spherical reamer without wobble, maintaining local predictable concentricity as the surgeon adjusts the reaming process.

U.S. Pat. No. 3,554,192 to Isberner discloses a medullary space drill. The medullary space drill includes a flexible shaft carrying at its opposite ends respectively a drill head, and an adapter piece adapted to be connected for rotation with a driving means. The shaft comprises a plurality of parallel flexible elements arranged to provide a central passage for receiving an elongated guide element. The medullary space drill disclosed by the '192 patent has a flexible shaft portion made from a plurality of circular rod or wire elements arranged in a circular fashion, forming a central hole for accommodating a guide pin. The bundle of rods or wires at the ends is jointed by welding or brazing, preserving the circular arrangement. When torsion is carried by the bundle of rods, there is a twist between the driven end and the reamer drilling end; the magnitude of the twist is a function of reaming torque needed. Thus, the twist may be irregular especially when the bone has hard and soft locations, thus delivering an unsteady torque. Also flexure of the flexible shaft portion requires some of the wire or rod elements of the bundle to move outward or inward and a single wire or rod may pop out of the circular arrangement if the flexure bend radius demanded is sharp. Even though the patent states that the flexible shaft is easy to clean, the bone fragments will dislodge and enter the central hole. Since the '192 patent contemplates cleaning of the flexible shaft, it is clearly not a disposable flexible shaft.

U.S. Pat. No. 4,362,520 to Perry, discloses a flexible enclosed shaft. This heavy-duty flexible shaft accommodates for misalignments between an input and output shaft. The flexible shaft is comprised of a multiplicity of hollow, individually fabricated, interfitting members housed in a tubular, bendable shaft. Each segment is intimately engaged, one within the other, yet the segments are so designed to allow for limited longitudinal movement while restricting circumferential movement between segments during torsion transmissions from the input to the output shafts. The flexible enclosed shaft disclosed by the '520 patent is a shaft designed for industrial use, but is not for medical use since it requires lubrication. The torque is delivered from the input shaft to the output shaft through the interfitting members. The cylindrical pipe merely serves to contain the interfitting members and does not carry any toque. The shaft does not accommodate a guide pin.

U.S. Pat. No. 4,541,423 to Barber discloses drilling a curved hole in bone tissue. This drilling apparatus is for attachment to a rotary motor that includes a flexible shaft confined in an elongated tubular sheath. The sheath is formed from a semi-rigid material which is bendable to a desired curvature, at the use site to select the curvature of the drilled hole, and which is rigid enough to retain that curvature in use. A drilling bit is fixed to one end of the flexible shaft, and includes a shank coacting with the distal end of the sheath to rotationally guide the drilling bit. The flexible shaft projects from the sheath at the proximal end so that both components may be secured to a drilling motor which is manipulated to guide the sheath while rotating the cutting bit. The sheath may remain in the drilled hole temporarily as a liner to guide the passage there through of a relatively stiff wire or other filamentary member. The sheath does not rotate and deliver the torque. Rather the spring-like flexible shaft resides inside the sheath and delivers the torque to the drill bit. The flexible shaft within the sheath is not indicated to accommodate a guide pin. Thus the drill bit and the reaming location is only controlled by the tip of the sheath, which is distal from the reaming location in the bone canal.

U.S. Pat. No. 4,706,659 to Matthews, et al. discloses a flexible connecting shaft for an intramedullary reamer. The flexible connecting shaft for an intramedullary reamer has several short segments or links are attached together to form an elongated flexible shaft. The shaft is designed to bend along its longitudinal axis while transmitting torque without any lag in such transmission, due to the specific attachment means for the links. A link at one end of the flexible shaft as made by a plurality of the links includes means provided for attachment to a torque providing device such as an electric motor. At the opposite end of the shaft, the last link includes structure thereon enabling connection to a drill bit. The plurality of short segments or links made of a material such as stainless steel, chrome cobalt-molybdenum alloy, titanium, or other metals. Each segment or link includes a male end and female end with each male end being specifically configured so as to interengage with the female end of an adjacent link. The links may be connected together to form a reamer shaft by inserting through the aligned holes in the individual links a flexible rod. This rod will hold the links together while allowing the flexing of the shaft about the longitudinal axis. The reamer shaft which will flex, curve or bend while transmitting torque and while at the same time reaming naturally curved long bones without cutting through the cortex or side wall of the bones. The links are only flexible at the joint locations and the inserted flexible shaft suffers piece wise bending, especially when the segment lengths are large. The flexing of the shaft requires free space between the links and as a result the torque transmission is not smooth in spite that the patent states that it is free lag in torque transmission. The flexible rod inserted does not function as a guide pin that guides the reamed bone cavity. The drill or reamer is not indicated to accommodate a guide pin and therefore the drilling or reaming location within a bone cavity can wander when the flexible shaft is flexed by the surgeon.

U.S. Pat. No. 4,751,922 and EP 0253526 to DiPietropolo disclose a flexible medullary reamer. The flexible medullary reamer is designed for shaping the medullary space of bones. The shaft is comprised of a single solid element. The flexible medullary rotational reamer for clearing, enlarging or otherwise modifying the medullary space of bones has a flexible shaft with a cutting head at one end and an adaptor piece at its opposite end for connecting said shaft to a rotational drive element, thereby causing rotation of the shaft. The shaft has a small diameter axial bore throughout its length to receive an elongated guide element. The flexible reamer shaft is a carbon fiber reinforced composite adapted for transmitting the torque from the drive mechanism to the drilling element while being still flexible. The torque transmission element has the high modulus carbon fibers embedded in low modulus polymer. Creating the composite and modulus mismatch does not provide smooth flexibility or torque transmission of the flexible shaft since the carbon fiber may delaminate from the surrounding polymer.

U.S. Pat. No. 5,122,134 to Borzone, et al. discloses a surgical reamer. The surgical reamer of the '134 patent uses a small flexible shaft to guide a reamer in an inclined orientation to enlarge a bone cavity. The reamer is guided by a guide pin. The flexible shaft in the drawing appears to be a shaft with spiral cuts. This type of shaft is expensive to make and hence is not commonly discarded after each operation and is subject to cross contamination since the flexible shaft with a central hole for a guide pin is not easy to clean.

U.S. Pat. No. 5,488,761 to Leone discloses a flexible shaft and method for manufacturing same. A shaft coupling for transmitting power includes a flexible hollow rod that extends in a longitudinal direction and has pairs of helical slots formed thereon. The flexible shaft can be rotated in both directions without jamming of the cutters. The flexible shaft of the '761 patent uses a machined helical pair or grooves to improve flexibility of the shaft. Such construction is hard and expensive to machine, and requires specialized machining techniques. The slots machined are required to be wide for effective cleaning. Due to this expensive machining process involved, the flexible shaft needs to be cleaned and reused and is not disposable. The attachment procedure for the electrical motor or the reamer head is not disclosed.

U.S. Pat. No. 5,908,423 to Kashuba, et al. discloses a flexible medullary reaming system. This apparatus for reaming a bone canal, such as the medullary canal of a femur, has a flexible shaft with a proximal end for engaging a rotary transmission source. The proximal end of a first reamer is coupled to the distal end of the flexible shaft to prepare the distal portion of the canal. The flexible medullary reaming system disclosed by the '423 patent comprises a flexible shaft to which a group of three reamers, first, second and third are attached. The first reamer reams the proximal portion of the bone canal; the second reamer reams the intermediate portion, while the third reamer reams the distal portion of the bone canal. The third reamer may be driven independent of the first two reamers. The flexible shaft is flexed from a straight configuration to position the third reamer to ream in an arc in a proximal portion of a bone. The apparatus further comprises a metaphyseal template having the shape of the prosthesis for guiding the reaming apparatus in forming the calcar region of the canal. The curvature of the medullary canal, as formed, rather than the angles formed according to the prior art, allows the implant shape to more closely match the curvature of the anatomy. This flexible shaft is of any design including a spirally wound shaft and is not indicated to be disposable.

U.S. Pat. No. 6,053,922 to Krause, et al. discloses a flexible shaft. This improved flexible shaft is used in the reaming of the medullary space in bones. The shaft is comprised of a solid element with a longitudinal bore the entire length and an appropriately formed slot which extends spirally around the shaft either continuously or segmentally. Attached to the shaft's opposite ends respectively, are a cutting head and a means of connecting the shaft to a driving mechanism. The flexible shaft of the '922 patent uses a spiral grooved solid shaft that can flex due to the interlocking segments that flex and transmit torque. The shaft has a central bore suited for a guide wire. Bone debris can easily get into the interlocking locations creating jamming of the flexible shaft. The process of making spiral grooves is expensive and the flexible shaft is not indicated to be disposable.

Foreign Patent Application Patent No. WO/2003/039378 to White discloses a drive shaft coupling and flexible surgical reamer. The reamer employs a fitting with a radially flexible member, e.g., a split collet or a super-elastic collar that receives an elongated tubular shaft of super-elastic alloy. A compression sleeve is applied to the collet, in one embodiment, while the collar is located within a counter-bore of the fitting in another embodiment. Relative motion between the shaft, fitting and collet (or collar) induces a super-elastic activation in the shaft to form the desired coupling. The drive shaft coupling and flexible surgical reamer of the '378 patent uses a super-elastic shaft made from nickel titanium alloy, Nitinol, which is a shape memory alloy. This Nitinol flexible shaft is expensive. It requires specialized heat treatment to provide shape memory properties, and thus is not disposable.

Non-Patent Document Flexible Reamers and Reaming Heads at www.chrispqld.com/easi_sterilise/flex_reamer.pdf discloses photographs of a flexible reamer. The shaft has a continuous helical groove, which enables flexible bending and torque transmission. The ends of the shaft are attached to a driving mechanism at one end and a cannulated reamer at the other end. The flexible shaft of the Flexible Reamers and Reaming Heads document uses a helical cut grooved solid shaft that can flex only at small flexure radius. Repeated flexing is indicated to result in loss of the reamer shaft shape. Bone fragments can get in between the helical cut portions, making the reamer very difficult to clean. The helical grooving is expensive; and therefore cleaning is anticipated. The flexible reamer shaft is therefore not disposable.

Non-Patent Document NT Flexible Reamer Shaft for Orthopaedic Application at http://www.fitec.co.jp/ftm/english/nt-e/reamer.htm discloses a flexible reamer shaft made from a shape memory alloy. When the shaft tube is bent, it returns back to its original shape. The ends of the shaft are attached to a driving mechanism at one end and a cannulated reamer at the other end. The flexible shaft of the NT Flexible Reamer Shaft document uses shaft metal alloy tube which can be flexed but returns to its original shape. The flexible shaft carries torque from the drive to the drill. This NT flexible shaft is expensive. It requires specialized heat treatment to provide shape memory properties, and thus is not disposable.

There remains a need in the art for a low-cost, disposable shaft that is capable of transmitting torque from the driving mechanism to a bone reamer. The disposable shaft must be flexible and enable reaming or cleaning of curved segments of a bone cavity without damaging bone tissue. The disposable nature of the low-cost flexible reamer will prevent cross contamination of bone debris, blood and tissue residues from patient to patient since cleaning of non-disposable flexible reamer shafts is usually difficult and unreliable.

SUMMARY OF THE INVENTION

The disposable flexible reamer shaft broadly includes, a flexible tube formed from cylindrically braided groups of wires forming a torque transmitting flexible tube shaft. Inside the braided wire tube structure a flexible polymeric tube is provided. The ends of the flexible braided tube are welded, brazed, crimped or glued to hardware that connects to a fitting. One end of the fitting is compatible with attachment to an electrical motor drive. The other end is adapted for attachment to a fitting that connects to a modular reamer that may be tapered, cylindrical or spherical, hollow or solid. This attachment is typically accomplished by a threaded connection having counter clockwise threads that do not loosen during the reaming procedure, or the attachment can be through a hex or square type fitting.

The present invention provides a disposable shaft for reamers. Reamer shafts are typically long with a shaft length in the range of 250 to 400 millimeters. These shafts have a small shaft diameter typically in the range of 4 to 14 millimeters, preferably 5 millimeters for modular hollow tattered reamers and 14 mm for attachment to a modular tapered, cylindrical or spherical, hollow or solid reamer. The shaft must have certain features for the concentric attachment of the disposable shaft with a modular reamer maintaining the local centerline of the shaft with that of the axis of rotation of the modular reamers attached. In this manner, the surgeon can clearly control the modular reamers with wobble-free rotation of the modular reamers. The modular reamer and the reamer shaft must be cannulated. By cannulated is meant that the reamer shaft has a central hole for inserting a guide pin. The guide pin inserted into the bone cavity provides the aiming point, and the exact orientation of the reamer. The guide pin provides one support for the reamer while the second support is provided by a long length threaded attachment of the modular reamer with the reamer shaft, as described herein below. This two-support attachment of the modular reamer to the flexible shaft precise local centerline matching of the rotation axis of the modular reamer with the local centerline of the flexible shaft at the modular reamer attachment end. The guide pin not only passes through the modular reamer but is supported within the annulus of the flexible reamer shaft within a flexible polymeric tube provided within the annulus of the cylindrically braided flexible reamer tubular shaft.

The disposable flexible reamer shaft for medical applications has two ends. A first end is adapted for attachment to a modular tapered, cylindrical or spherical, hollow or solid reamer. The second end is adapted for attachment to a motor drive. Both of these reamers have female threads at the proximal end where they attach to the disposable flexible reamer shaft. The threads are generally oriented in the counter clockwise direction, so that the threads do not loosen during the reaming operation. These modular tapered hollow reamers, as well as spherical hollow reamers, are detailed in pending application Ser. No. 11/704,754, filed Feb. 9, 2007, Ser. No. 11/973,260, filed Oct. 5, 2007 and Ser. No. 12/072,2671, filed on Feb. 27, 2008, the disclosures of which are hereby incorporated in their entirety by reference thereto. These reamers have a central aperture to accept a guide pin.

The attachment of the modular tapered, cylindrical or spherical, hollow or solid, reamer to the distal end threads of the disposable flexible reamer shaft is a single point attachment and relies on the threaded length provided to maintain local concentricity of the shaft. Since the shaft is flexible, the only issue that matters is the local concentricity. The surgeon can reliably guide the shaft along any orientation as long as the reamer follows exactly the orientation selected by the surgeon. In such cases, the reamer aim point is precisely determined by the insertion point of the guide pin within the bone cavity. This process of orienting the shaft and the reamer is aided by the previously inserted guide pin in the bone cavity, so that the surgeon can readily orient the reamer within the bone cavity. The flexible shaft may be used for creating a fresh bone cavity or for enlarging an existing bone cavity.

When a modular hollow reamer is used with the flexible shaft, it captures the bone debris and moves it away from the cutting location, thereby reducing heat build up at the reaming surface. This prevents damage to bone tissue and promotes rapid bone healing. Since the shaft is a low-cost construction, it can be disposed off readily, thus preventing cross contamination.

The low-cost disposable flexible reamer shaft for a disposable spherical or tapered hollow reamer for medical applications comprises:
i. a flexible cylindrically braided shaft in the form of a tube that carries torque;
ii. the cylindrical braided shaft having a first end element with male screw threads of length sufficient for attachment to a modular tapered, cylindrical or spherical, hollow or solid, reamer;
iii. the male element screw threads being counter clockwise, thereby preventing loosening of the modular reamer during the bone reaming procedure;
iv. the cylindrically braided shaft having a second end element with matching fittings to accept a motor drive shaft;
v. the first and second end elements being attached to a cylindrically braided shaft by welding, brazing, crimping or gluing;
vi. said braided cylindrical shaft having a central aperture that carries a polymeric flexible tube element; and
vii. a guide pin affixed to the bone cavity entering said modular reamer and extending into the polymeric tube element with close diametrical tolerance setting the direction of reaming action, as guided by the surgeon;
viii. whereby a surgeon guides the low-cost disposable flexible shaft with the modular reamer guided to reach a precise aim point within bone cavity, as set by the selected guide pin location within the bone cavity along a reaming direction selected by the surgeon.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

In orthopedic surgery, many surgical procedures require the need to ream the internal cavity of long bones. These include fracture procedures and total hip procedures. In the current technology, rigid solid reamers and flexible reamers are used for preparing the bone canals for implants. These reamers can be one-piece construction and also modular allowing for the cutting head to be removed and different diameter sizes attached. Cutters can become dull even after one use and the option to discard the cutter would provide a significant benefit for the surgeon and the patient. It would assure that the cutters are always sharp and clean for each patient.

The reamer shafts, especially flexible shafts, which are designed to drive these cutters are typically reused. Although the sharpness of cutting teeth is not an issue, the ability to properly clean these reamer shafts is an issue. Many of the reamer shafts are cannulated with a small hole running down the center of the shaft, which allows blood, bone and other biologic matter to be captured within the shaft. It can be very difficult to remove and properly clean this type of contaminated shaft. If it is not properly cleaned it can become a potential infection problem when it is used on the next patient.

The disposable flexible reamer shaft of the present invention is directed towards meeting the following objectives:
1. Assure that the patient always has a clean, sterile reamer shaft;
2. Eliminate the need to clean a reamer shaft;
3. Eliminate the potential for infection from contamination through biologic debris; and
4. Assure the quality and function of the reamer shaft is always consistent for the patient.

A disposable flexible reamer shaft must accomplish several design objectives in order to provide the proposed benefits to the patient. These include:
1. Ability to flex in order to accommodate the curvature of the bone canal;
2. Cannulated, a hole running through the center, to accept a guide rod and thereby maintain positional control of the reamer shaft down the canal of the bone preventing the cutter from migrating out the cortical wall of the bone;
3. Strong enough to flex but still capable of transmitting the required torque to the cutter;
4. One end having a drive fitting to be assembled to a power tool;
5. Other end having a modular fitting which provides for the attachment of multiple sized cutters and which maintains cutter concentricity to the reamer shaft;
6. Assembly of the flexible reamer shaft, which provides for forward and reverse motion; and
7. Cost-effective method of manufacturing that meets the functional requirements but is also disposable, thereby eliminating the potential biohazard from attempting to clean/reuse a flexible reamer shaft.

The present invention uses a cylindrically braided tubular shaft that is flexible and carries the torque from the drive end to the reamer. The cylindrical braiding is well known in the art and it uses four or more fine diameter wires handled as a ribbon and braided, with an individual group of wire ribbons supporting each other. As a result of this nested self-supporting structure, the braided cylindrical tube can transmit torque without any slack and can flex without any wires coming loose or extending further from the braided construction. All that happens during flexing is the gap between wires in the ribbon separate out ever so slightly to accommodate the flexure of the cylindrically braided shaft construction. The ends of the cylindrically braided tubular shaft are fitted with a male counter clockwise screw thread connection element at the first end and a motor shaft attachment element at the second end. At the first end, the counter clockwise male screw threads attach to female threads provided in a modular tapered, cylindrical or spherical, hollow or solid reamer, that is provided with a central aperture for receiving a guide pin. The connection of these fittings to the cylindrically braided tubular shaft can be accomplished by means including welding, brazing, crimping or gluing. A polymeric flexible tube fits inside the central aperture of the cylindrical braided tubular shaft with the outer surface of the polymeric tube intimately contacting the interior surface of the cylindrically braided tubular shaft. The polymeric tube thus prevents bone debris from entering into the interior of the cylindrically braided tubular shaft. The inside diameter of the polymeric flexible tube is a clearance fit to a stainless steel guide pin that passes through the reamer. The guide pin is generally long and is initially affixed within a bone cavity setting the reaming aiming point and reaming direction. The polymeric flexible tube glides over the guide pin that passes through the modular reamers attached to the disposable flexible shaft with a low coefficient friction generating minimal polymeric debris. Thus the reaming direction is controlled by two support locations. First the threaded length of the male threads on the first end of the cylindrically braided shaft provides a long wobble-free, precise connection to the modular reamers. Secondly, the guide pin affixed within the bone cavity sets the direction and location of the reaming procedure and is clearance contact with the end of the reamer and the polymeric flexible tube setting the local centerline of the flexible shaft at the reaming end. The surgeon can adjust the reaming direction by merely flexing the flexible shaft and the reamer orientation is immediately followed along with the orientation of the guide pin. The reamer aim location is still determined by the inserted guide pin location even thought the orientation of the reaming direction may be changed by the surgeon by flexing the flexible reamer shaft. The reamer follows the precise orientation due to the local concentricity of the reamer rotation axis with that of the first end of the flexible reamer shaft.

Figure 1:
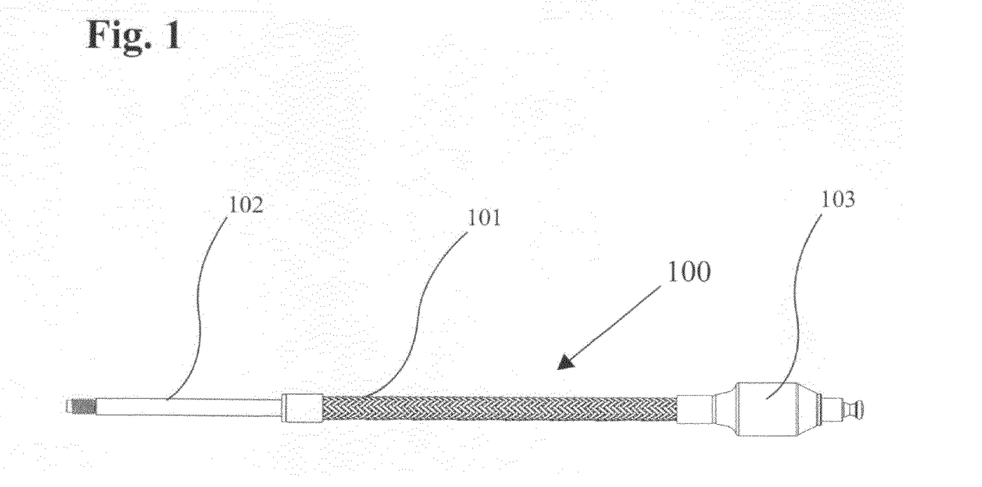
FIG. 1 Illustrates an assembled view of the disposable flexible reamer shaft for medical applications according to the subject invention.

FIG. 1 illustrates the flexible disposable reamer shaft assembly at 100. The reamer shaft comprises a central braided tube shaft portion 101 which is attached to a fitting 102 at the first end that attaches to a the female screw threads of a modular tapered, cylindrical or spherical, hollow or solid, reamer. The second end of the central braided tube shaft is attached to a fitting 103 that attaches to a motor drive. These components can be made of the same material or different materials. Assembly would require the ends 102 and 103 attached to the cylindrically braided tubular shaft using welding, brazing crimping or glued with for example epoxies to maintain a strength level capable of withstanding the torsional, stresses, bending stresses, tensile loads and compressive loads which it would be subjected to during a normal surgical procedure such as a total hip replacement surgery or repair of a fractured bone. Inside the cylindrically braided tube shaft there is a flexible polymeric tube the outer diameter of which contacts the interior of the cylindrically braided tube shaft. The joining processes such as welding or brazing generate heat and the flexible polymeric tube needs to be protected during this joining operation. This can be done by segmenting the inner polymeric tube, displacing it away from heated zone and pushing it back to the desired location. Joining methods such as crimping or gluing do not have this heat related problem.

In a preferred embodiment, the flexible reamer shaft is composed of an inner flexible polymeric tube inserted inside a stainless steel cylindrically braided flexible tube shaft with crimped end fittings using crimp sleeves. This construction allows adequate torque transmission, flexibility and also assurance that with a shaft failure, the flexible inner tube will not fragment into several pieces while in the canal of the bone. The design of the braided cylindrical flexible tube shaft and an inner plastic tube work in conjunction to provide strength and flexibility.

Figure 2:
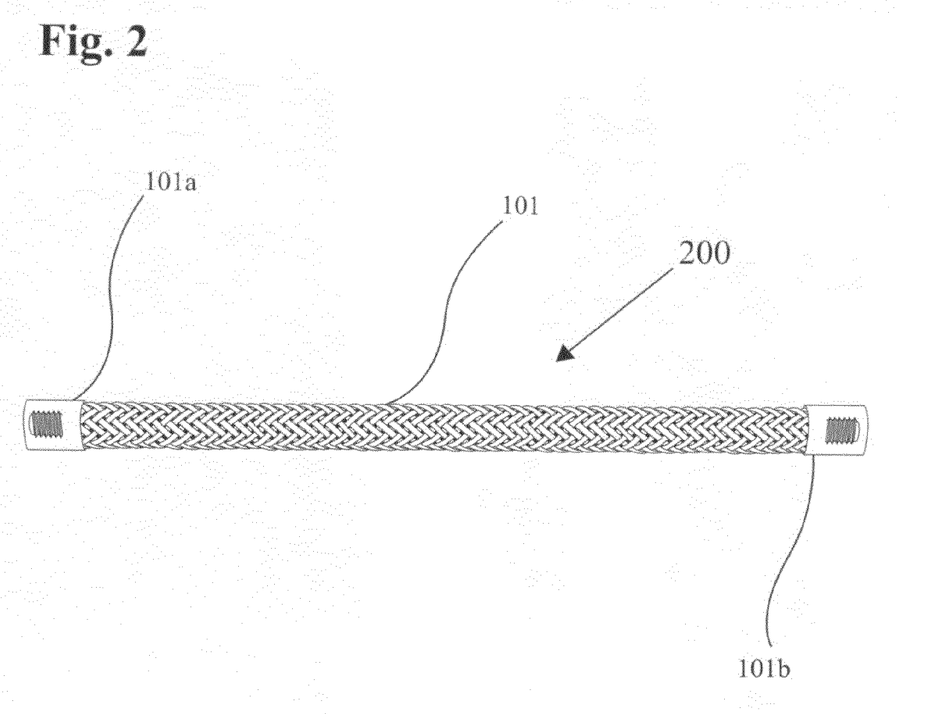
FIG. 2 Illustrates the cylindrically braided tube shaft central portion of the disposable flexible reamer shaft.

FIG. 2 Illustrates at 200 cylindrically braided tube shaft central portion 101 of the disposable flexible reamer shaft. The end 101*a* is used to attach to a male threaded fitting for attachment to a modular reamer. The end 101*b* is used to attach to a fitting for attachment to a drive such as an electrical motor shaft. These fittings are inserted into the ends of the cylindrically braided tube shaft central portion 101 and crimped using a crimping sleeve as shown in FIG. 1.

Figure 3:
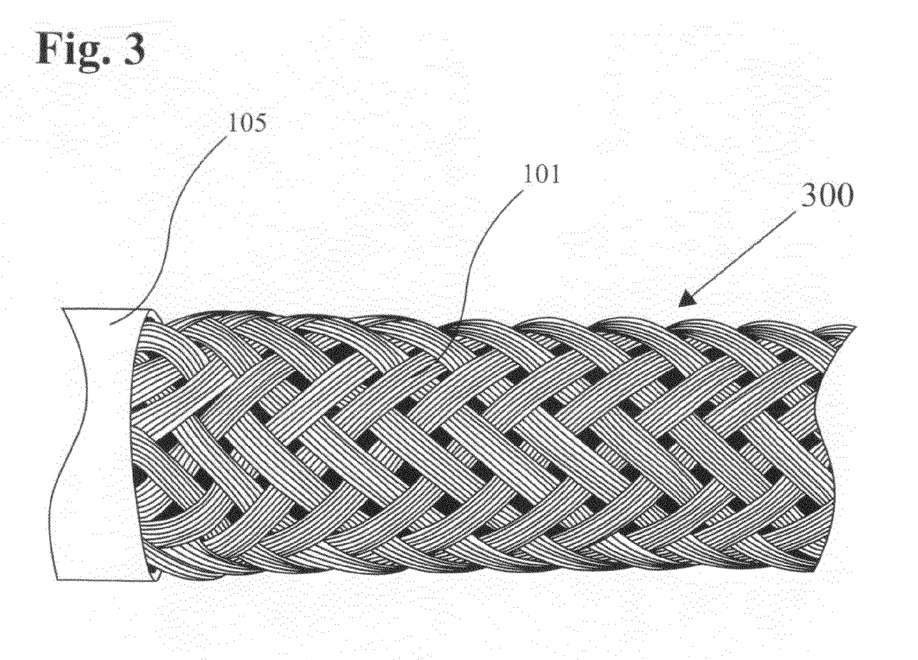
FIG. 3 Illustrates the details of the cylindrically braided tube shaft central portion showing braided bundle of wires and the crimping sleeve.

FIG. 3 Illustrates at 300 a photograph of the braiding details of the cylindrically braided tube shaft central portion 101 of the disposable flexible reamer shaft. The braided portion has seven wires held flat in the form of a ribbon and cylindrically braided as shown. The end of the cylindrically braided tube shaft central portion 101 is held together permanently by a crimping sleeve 105.

Figure 4:
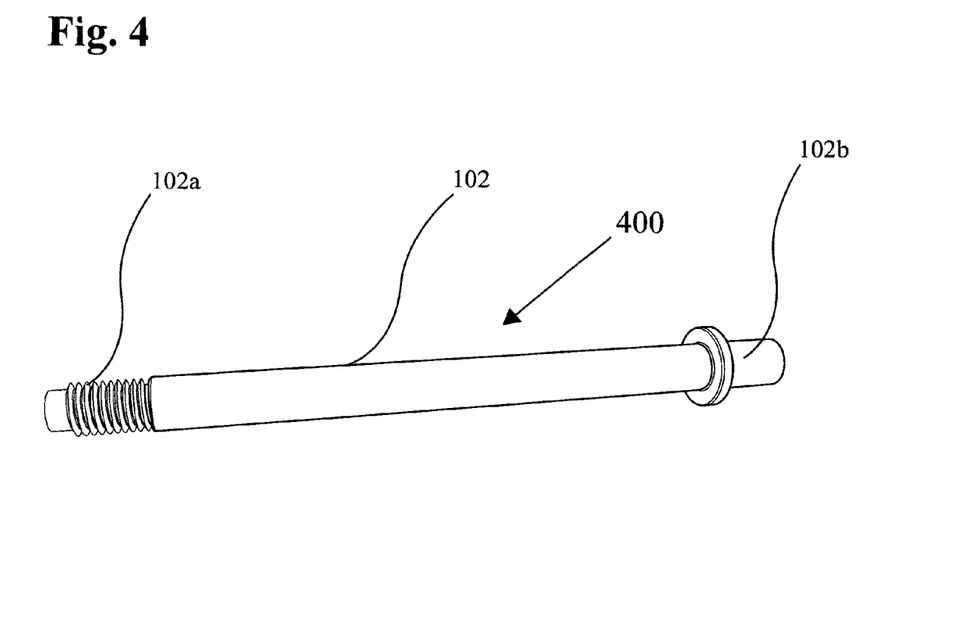
FIG. 4 Illustrates the fitting at the first end fitting of the disposable flexible reamer shaft that screws into a modular reamer.

FIG. 4 Illustrates at 400 the fitting 102 at the first end of the cylindrically braided tube shaft 101 of FIG. 1 or 2 for the screwed attachment of the modular reamer to the disposable flexible reamer shaft. The end shown at 102*a* shows a male screw thread that is threaded in the counter clockwise direction. The central tube shown at 102*a* has an aperture for the guide pin insertion that passes through the central aperture provided in the modular reamer. The end shown at 102*b* is inserted into the central opening at 101*a* of the cylindrically tubular braided central shaft portion and crimped using a crimp sleeve as shown in FIG. 1.

Figure 5:
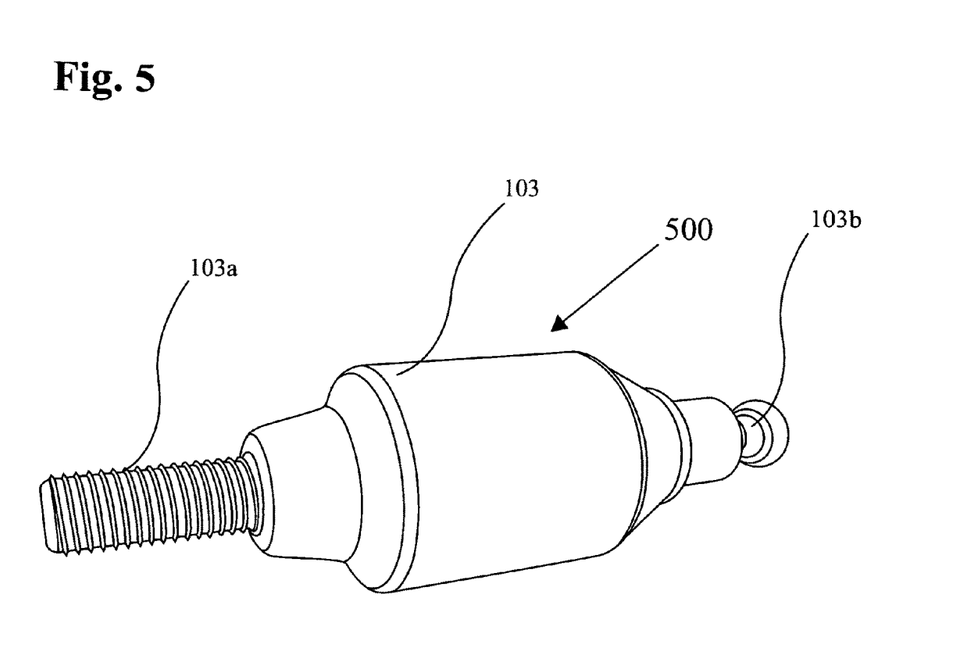
FIG. 5 Illustrates the fitting at the second end of the disposable flexible reamer shaft that attaches to a drive device.

FIG. 5 Illustrates at 500 the fitting 103 at the second end of the cylindrically braided tube shaft 101 of FIG. 1 or 2 for the attachment to a drive shaft of electrical motor drive. The fitting 103 has the first end 103*a*, which is inserted into the central opening at 101*b* of the cylindrically tubular braided central shaft portion after the insertion of the close fitting polymeric flexible tube. A crimp sleeve is used to complete the attachment of 103 into the second end of cylindrically braided tube shaft 101 as shown in FIG. 1. The second end 103*b* of the fitting 103 has a protruding shaft for attachment to a chuck provided on the drive shaft of an electric motor.

The key features of the low cost disposable flexible reamer shaft for medical applications include, in combination, the components set forth below:
  a) a flexible cylindrically braided shaft in the form of a tube that carries torque;
  b) said cylindrical braided shaft having a first end element with a male screw threads of sufficient length for attachment to a modular tapered, cylindrical or spherical, hollow or solid, reamer;
  c) said male element screw threads being counter clockwise, and thereby preventing loosening of the modular reamer during the bone reaming procedure;
  d) said cylindrically braided shaft having a second end element with matching fittings sized to fit to a chuck of a power drive;
  e) the first and second end elements are attached to cylindrically braided shaft by welding, brazing, crimping or gluing;
  f) said braided cylindrical shaft having a central aperture that carries a polymeric flexible tube element with a central aperture; and
  g) a guide pin affixed to bone cavity, the guide pin entering a central aperture of said modular reamer and extending into the polymeric tube element with close diametrical tolerance, thereby setting the direction of reaming action as guided by the surgeon;

whereby a surgeon guides said low cost disposable flexible shaft with the modular reamer guided to reach a precise aim point within bone cavity as set by the selected guide pin location within the bone cavity along a reaming direction selected by the surgeon, whereby the local centerline of the low cost disposable flexible reamer shaft at the first end of the reamer attachment is concentric to the centerline of the modular reamer, providing wobble-free reaming action.

The manufacturing process for the low cost disposable flexible reamer shaft for medical applications comprises the following manufacturing steps;
  1. cylindrically braiding a tube shaft with an outer diameter in the range of 4 to 14 millimeters having a first end and a second end;
  2. providing a machined first end fitting with a central aperture for a guide pin;
    a. said first end fitting having a first end having male threads in counter clockwise direction for attachment to modular reamer female threads;
    b. said first end fitting having a second end having attachment features for connecting to said first end of a cylindrically braided tube shaft;
  3. providing a machined second end fitting with a central aperture for a guide pin;
    a. said second end fitting having a first end having attachment features for connecting to said first end of a cylindrically braided tube shaft;
    b. said second end fitting having a second end having attachment features for connecting to a motor drive shaft;
  4. providing a polymeric flexible tube having an inside aperture closely fitting on a guide pin used to guide the flexible shaft and having an outer diameter closely fitting the inside aperture of the cylindrically braided tube shaft;

5. inserting said polymeric flexible tube inside the inside aperture of the cylindrically braided tube shaft;
6. inserting and permanently attaching said machined first end fitting into the first end of said cylindrically braiding a tube shaft;
7. inserting and permanently attaching said machined second end fitting into the second end of said cylindrically braiding a tube shaft;

whereby said low cost disposable flexible reamer shaft for medical applications with cannulation is fabricated from stainless steel, Nitinol or flexible metallic material.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A low cost disposable flexible reamer assembly for medical applications, comprising:
   a. a torque transmitting flexible cylindrically braided shaft in the form of a tube having a first end and second end, said cylindrically braided shaft being metallic;
   b. said first end of the flexible cylindrically braided shaft having a bonded first end element with male screw threads of sufficient length for attachment to said modular reamer assembly;
   c. said male element screw threads being counter clockwise, to prevent loosening of said modular reamer assembly during the bone reaming procedure;
   d. said flexible cylindrically braided shaft having a bonded second end element with a matching fitting sized to fit to a chuck of a power drive;
   e. said cylindrically braided shaft having a central aperture that carries a polymeric flexible tube element with a central aperture, said polymeric flexible tube element extending through said cylindrically braided shaft;
   f. a guide pin adapted to be affixed to a bone cavity, the guide pin being adapted to enter a central aperture of said modular reamer assembly and extend into the central aperture of polymeric tube element with close diametrical tolerance, and to set the direction of reaming action as guided by the surgeon; and
   g. said reamer being hollow;

whereby a surgeon guides said low cost disposable flexible shaft with said modular reamer to reach a precise aim point within the bone cavity set by the guide pin positioned along the reaming direction selected by the surgeon.

2. A low cost disposable flexible reamer assembly for medical applications as recited by claim 1, wherein said cylindrically braided tube shaft has an outer surface diameter in the range of 4 mm to 14 mm.

3. A low cost disposable flexible reamer assembly for medical applications as recited by claim 1, wherein said cylindrically braided tube shaft has a length in the range of 250 mm to 400 mm.

4. A low cost disposable flexible reamer assembly for medical applications as recited by claim 1, wherein said cylindrically braided tube shaft is made from braided stainless steel or braided metallic flexible fibers.

5. A low cost disposable flexible reamer assembly for medical applications as recited by claim 4, wherein said cylindrically braided tube shaft is made from braided Nitinol.

6. A low cost disposable flexible reamer assembly for medical applications as recited by claim 1, wherein said first end element and second end element of the flexible cylindrically braided shaft are bonded to said first end and said second end respectively by glue.

7. A low cost disposable flexible reamer assembly for medical applications as recited by claim 6 wherein the glue is epoxy resin.

8. A low cost disposable flexible reamer assembly for medical applications as recited by claim 1, wherein said first end element and said second end element of said flexible cylindrically braided shaft are bonded to said first end and said second end respectively by crimping, using a crimping sleeve.

9. A low cost disposable flexible reamer assembly for medical applications as recited by claim 1, wherein said first end element and said second end element of said flexible cylindrically braided shaft are bonded to said first end and said second end respectively by welding.

10. A low cost disposable flexible reamer assembly for medical applications as recited by claim 1, wherein said first end element and said second end element of said flexible cylindrically braided shaft are bonded to said first end and said second end respectively by brazing.

11. A low cost disposable flexible reamer assembly as recited by claim 1, wherein said reamer is tapered.

12. A low cost disposable flexible reamer assembly as recited by claim 1, wherein said reamer is spherical.

* * * * *